(12) United States Patent
Bairstow

(10) Patent No.: US 8,865,412 B2
(45) Date of Patent: Oct. 21, 2014

(54) METHODS AND ASSAYS FOR OVERSULFATED GLYCOSAMINOGLYCANS

(75) Inventor: Shawn F. Bairstow, Gurnee, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1294 days.

(21) Appl. No.: 12/128,101

(22) Filed: May 28, 2008

(65) Prior Publication Data

US 2009/0298705 A1    Dec. 3, 2009

(51) Int. Cl.
*G01N 33/53* (2006.01)
*C40B 30/04* (2006.01)
*G01N 33/566* (2006.01)
*A61K 31/727* (2006.01)

(52) U.S. Cl.
CPC .......... *G01N 33/566* (2013.01); *G01N 2400/40* (2013.01)
USPC ............ 435/7.1; 435/7.8; 435/7.93; 436/500; 506/9; 514/54; 514/56

(58) Field of Classification Search
USPC ............. 435/7.1; 436/500; 506/9; 514/54, 56
See application file for complete search history.

(56) References Cited

U.S. PATENT DOCUMENTS

2005/0239155 A1  10/2005  Alarcon et al.
2008/0025950 A1   1/2008  Prestwich et al.

FOREIGN PATENT DOCUMENTS

WO   WO 2005/018552  *  3/2005
WO   WO 2005018552      3/2005
WO   WO2006105313      10/2006

OTHER PUBLICATIONS

Hindson et al. (Opticin binds to heparin and chondroitin sulfate proteoglycans, Investigative Opthalmology and Visual Science, 2005, vol. 46, pp. 4417-4423).*
Garcia-Olivas et al. (Differential binding of platelet-derived growth factor isoforms to glycosaminoglycans, 2003, Histochemistry and Cell Biology, vol. 120, pp. 371-382).*
Deepa et al. (Specific molecular interactions of oversulfated chondroitin sulfate E with various heparin-binding growth factors, 2002, The Journal of Biological Chemistry, vol. 277, pp. 43707-43716).*
Ashikara et al. (Characterization of growth factor-binding structures in heparin/heparan sulfate using an octasaccharide library, 2004, The Journal of Biological Chemistry, vol. 279, pp. 12346-12354).*
Bairstow et al. (Identification of a simple and sensitive microplate method for the detection of oversulfated chondroitin sulfate in heparin products, 2009, Analytical Biochemistry, vol. 388, pp. 317-321).*
Nandini et al. (Structural and functional characterization of oversulfated chondroitin sulfate/dermatan sulfate hybrid chains from the notochord hagfish, 2004, The journal of Biological Chemistry, vol. 279, pp. 50799-50809).*
T. Kishimoto et al., "Contaminated Heparin Associated with Adverse Clinical Events and Activation of the Contact System," The New England Journal of Medicine, vol. 358, No. 23, Apr. 2008, pp. 2457-2467.
M. Guerrini, et al., "Oversulfated chondroitin sulfate is a contaminant in heparin associated with adverse clinical events," Nature Biotechnology, Apr. 2008, pp. 1-7.
S. Cai, et al., "A selective protein sensor for heparin detection," Analytical Biochemistry, vol. 326 (2004), pp. 33-41.
A. Gardner, "Researchers Identify Contaminant in Tainted Heparin; More testing is needed to prove that oversulfated chondroitin sulphate caused deaths, reactions," posted on Apr. 23, 2008 U.S. News & World Report website, downloaded from http://health.usnews.com/usnews/health/healthday/080423/researchers-identify-contaminant-in-tainted-heparin.htm on May 2, 2008.
S. Deepa et al., "Specific molecular interactions of oversulfated chondroitin sulfate E with various heparin-binding growth factors: Implications as a physiological binding partner in the brain and other tissues," downloaded from www.jbc.org on May 5, 2008, pp. 1-44.
Soeda et al., "Inhibitory Effect of Oversulfated Fucoidan on Invasion through Reconstituted Basement Membrane of Murine Lewis Lung Carcinoma," Jpn. J. Cancer Res., vol. 85, Nov. 1994, pp. 1144-1150.
Kawashima et al., "Oversulfated Chondroitin/Dermatan Sulfates Containing GldAβ1/IdoAalpha1-3GalNAc(4,6-O-disulfate) Interact with L- and P-selectin and Chemokines*," The Journal of Biological Chemistry, vol. 277, No. 15, Issue of Apr. 12 (2002), pp. 12921-12930.
Sorrell et al., "A monoclonal antibody which recognizes a glycosaminoglycan epitope in both dermatan sulfate and chondroitin sulfate proteoglycans of human skin," The Histochemical Journal, vol. 31, (1999), pp. 549-558.

(Continued)

*Primary Examiner* — Amber D. Steele
*Assistant Examiner* — Shannon Janssen
(74) *Attorney, Agent, or Firm* — K&L Gates LLP

(57) ABSTRACT

Methods and assays for oversulfated glycosaminoglycans are provided. In an embodiment, the present disclosure provides a method for detecting oversulfated glycosaminoglycan (OS-GAG) in a heparin sample. The method comprises placing the heparin sample onto a support comprising immobilized heparin and contacting the heparin sample on the support with a binding compound that attaches to the heparin and forms a heparin-binding compound complex. The binding compound also has a greater affinity for attaching to the OS-GAG than to the heparin in the heparin sample and forms an OS-GAG-binding compound complex. The method can further comprise detecting an amount of the heparin-binding compound complex on the support, and determining an amount of OS-GAG in the heparin sample based on the amount of the heparin-binding compound complex on the support.

15 Claims, 6 Drawing Sheets

(56) References Cited

OTHER PUBLICATIONS

Kawashima et al., "Binding of a Large Chondroitin Sulfate/Dermatan Sulfate Proteoglycan, Versican, to L-selectin, P-selectin, and CD44*," vol. 275, No. 45, Issue of Nov. 10 (2000), pp. 35448-35456.

Barbosa et al., "Improved and simple micro assay for sulfated glycosaminoglycans quantification in biological extracts and its use in skin and muscle tissue studies," Glycobiology, vol. 13, No. 9, (2003), pp. 647-653.

Guimaraes et al., Urinary excretion of sulfated polysaccharides administered to Wistar rats suggests a renal permselectivity to these polymers based on molecular size, Biochimica et Biophysica Acta 1335 (1997), pp. 161-172.

International Search Report for PCT/US2009/045385 filed May 28, 2008, 8 pages.

Written Opinion of the International Searching Authority for PCT/US2009/045385 mailed May 28, 2008, 10 pages.

* cited by examiner

METHODS AND ASSAYS FOR OVERSULFATED GLYCOSAMINOGLYCANS

BACKGROUND

The present disclosure is generally directed to analytical methods for chemical compounds. More specifically, the present disclosure is directed to methods and assays for detecting and/or removing oversulfated glycosaminoglycan.

Heparin is an anticoagulant that is used in many applications such as in surgery of the heart and blood vessels, with organ transplants and artificial organs, for cardiovascular diagostic techniques, and for the control and prevention of thromboembolism following surgical operations. Heparin is a polysaccharide not having a uniform molecular structure. It is generally considered a mixture of polymers of varying size and slight differences exist between the polymers and in the individual sugars within a particular polymer grouping.

It has recently been reported that heparin batches have been contaminated with oversulfated chondroitin sulfate. Chondroitin sulfate is a glycosaminoglycan. Oversulfated chondroitin sulfate is a man-made chemical contaminant that has been linked to allergic reactions in patients receiving the contaminated heparin. Oversulfated chondroitin sulfate mimics heparin's qualities and is a modified form of chondroitin sulfate. Chondroitin sulfate is a naturally occurring substance made from animal cartilage and is often used in supplements to treat arthritic joints.

SUMMARY

The present disclosure is directed to methods and assays for detecting and/or removing oversulfated glycosaminoglycan (OS-GAG) in various products. The OS-GAG can be, for example, oversulfated chondroitin sulfate (OSCS), oversulfated dermatan sulfate, oversulfated heparin sulfate, oversulfated heparan sulfate, oversulfated hyaluronic acid or oversulfated keratan sulfate. In a general embodiment, the present disclosure provides a method for detecting one or more OS-GAGs in a sample. The method comprises placing the sample onto a support, contacting the sample on the support with a binding compound that attaches to the OS-GAG and forms an OS-GAG-binding compound complex, and detecting an amount of the OS-GAG-binding compound complex on the support.

As used herein, the term "binding compound" means any molecule that binds to an OS-GAG. In an embodiment, the binding compound comprises an OS-GAG binding unit. In another embodiment, the binding compound comprises a heparin binding construct having an affinity for OS-GAG. The OS-GAG binding unit/heparin binding construct can further be fused or bound to a component such as an enzyme, an antibody or a combination thereof for detection/identification. Alternatively, the OS-GAG binding unit/heparin binding construct can be labeled with a component such as a fluorescent molecule, a radionuclide, biotin or a combination thereof for detection/identification.

The samples can be, for example, a biological sample such as heparin. In an embodiment, the support comprises OS-GAG attached to the support. The support can be a microtiter plate, a microassay chip or a combination thereof.

In another embodiment, the present disclosure provides a method for detecting one or more OS-GAGs in a heparin sample. The method comprises placing the heparin sample onto a support comprising immobilized heparin and contacting the heparin sample on the support with a binding compound that attaches to the heparin and forms a heparin-binding compound complex. The binding compound also has a greater affinity for attaching to the OS-GAG than to the heparin in the heparin sample and forms an OS-GAG-binding compound complex. The method can further comprise detecting an amount of the heparin-binding compound complex on the support, and determining an amount of OS-GAG in the heparin sample based on the amount of the heparin-binding compound complex on the support.

In an alternative embodiment, the present disclosure provides an OS-GAG assay comprising a support comprising one or more immobilized OS-GAGs, and a binding compound that attaches to the OS-GAG immobilized on the support and forms an OS-GAG-binding compound complex. The support can be in the form of a microtiter plate, a microassay chip or a combination thereof. The binding compound can comprise a heparin binding unit. In an embodiment, the binding compound is an HB3 construct.

In yet another embodiment, the present disclosure provides a method for detecting one or more OS-GAGs in heparin. The method comprises applying the heparin to an assay. The assay can utilize a binding compound that attaches to the OS-GAG in the assay to form an OS-GAG-binding compound complex. The method can further comprise detecting the OS-GAG-binding compound complex in the assay. The detecting can be performed using a calorimetric assay, a fluorescence assay, bioluminescence assay, and/or radiolabeled assay.

In still another embodiment, the present disclosure provides a method for detecting one or more OS-GAGs in a sample. The method comprises providing a support having heparin bound to the support and combining the sample with a heparin binding reagent on the support. The heparin binding reagent comprises a binding compound that attaches to the heparin on the support and forms a heparin-binding compound complex. The binding compound has a greater affinity for attaching to the OS-GAG in the sample than the heparin on the support and forms an OS-GAG-binding compound complex. The method can further comprise incubating the sample with the heparin binding reagent to allow for the formation of the heparin-binding compound complex and the OS-GAG-binding compound complex, washing the support to remove the heparin binding reagent, apply a substrate to the support to elicit signal, and detecting the strength of the signal to determine the presence of the OS-GAG in the sample.

The signal can be a chromogenic signal, a fluorogenic signal, an electrochemical signal or a combination thereof. Detecting the strength of the signal can be performed using an instrument such as a spectrophotometer and a spectrofluorometer.

In an alternative embodiment, the present disclosure provides a method of removing one or more OS-GAGs from a sample. The method comprises immobilizing a binding compound that attaches to the OS-GAG, and exposing the binding compound to the sample under conditions that allow for an OS-GAG-binding compound complex formation. The sample can be, for example, heparin, plasma, blood, some other biological sample or a combination thereof.

The binding compound can be immobilized onto any suitable surface. In an embodiment, the binding compound is immobilized by adsorbing it to a solid-phase support such as, for example, activated beads. The binding compound can also be immobilized to a microtiter plate or a microassay chip.

In yet another embodiment, the present disclosure provides a method of using heparin. The method comprises applying the heparin to an assay. The assay can be an enzyme assay that utilizes a binding compound that attaches to an OS-GAG in the heparin to form an OS-GAG-binding compound complex.

The method can further comprise detecting the OS-GAG-binding compound complex in the assay, and using the heparin as an anticoagulant.

In still another embodiment, the present disclosure provides a method of manufacturing heparin. The method comprises contacting the heparin with a binding compound that attaches to an oversulfated glycosaminoglycan (OS-GAG) in the heparin to form an OS-GAG-binding compound complex. The method can further comprise removing the OS-GAG-binding compound complex from the heparin. The binding compound can be immobilized on a support such as solid-phase support, a microtiter plate, a microassay chip and combinations thereof.

In an alternative embodiment, the present disclosure provides a compound comprising an oversulfated chondroitin sulfate-binding compound complex formed by a binding compound attached to oversulfated glycosaminoglycan such as, for example, oversulfated chondroitin sulfate or oversulfated heparin.

In still another embodiment, the present disclosure provides a method for manufacturing OS-GAG comprising contacting an OS-GAG in a carrier with a binding compound that attaches to the OS-GAG to form an OS-GAG-binding compound complex. The method can further comprise removing the OS-GAG-binding compound complex from the carrier. The binding compound can comprise a heparin binding unit such as an HB3 construct.

In yet another embodiment, the present disclosure provides for a chemical binding apparatus comprising a binding compound attached to a support. The binding compound is capable of attaching to an OS-GAG to form an OS-GAG-binding compound complex. The support can comprise one or more microspheres with the binding compound attached to the microspheres.

An advantage of the present disclosure is to provide an improved method for detecting oversulfated glycosaminoglycans.

Another advantage of the present disclosure is to provide an improved method for detecting a contaminant in heparin.

Yet another advantage of the present disclosure is to provide an improved assay for detecting oversulfated glycosaminoglycans.

Still another advantage of the present disclosure is to provide an improved method of removing oversulfated glycosaminoglycans from a sample.

Another advantage of the present disclosure is to provide an improved method of using heparin.

Yet another advantage of the present disclosure is to provide an improved method of manufacturing heparin.

Additional features and advantages are described herein, and will be apparent from the following Detailed Description and the figures.

DETAILED DESCRIPTION

Figure 1:
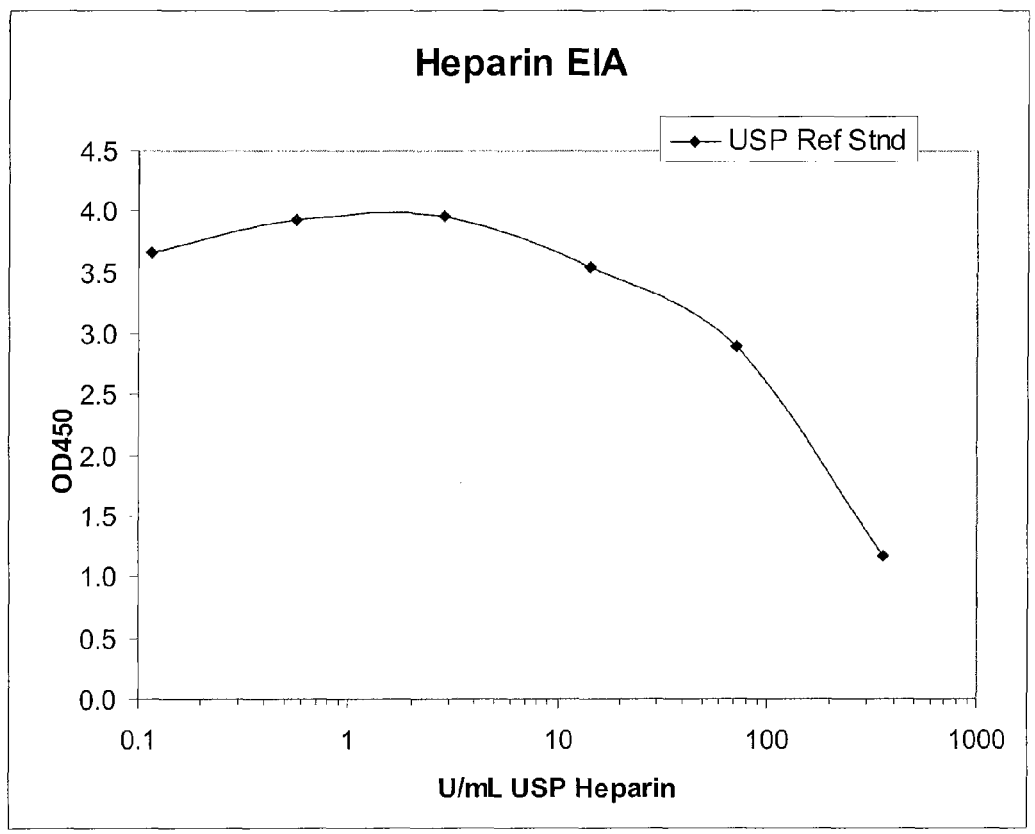
FIG. 1 shows a graph of a response curve for a Heparin Reference Standard (357 U/mL—U.S. Pharmacopeia).

The present disclosure is directed to methods and assays for detecting and/or removing oversulfated glycosaminoglycan in various products such as pharmaceutical and nutritional products. The OS-GAG can be, for example, oversulfated chondroitin sulfate, oversulfated dermatan sulfate, oversulfated heparin sulfate, oversulfated heparan sulfate, oversulfated hyaluronic acid or oversulfated keratan sulfate.

The methods and assays in embodiments of the present disclosure can provide for rapid and relatively inexpensive screening of samples for oversulfated OS-GAG. The samples can be, for example, any size portion of one or more biological or pharmaceutical products or products for human or animal administration/consumption. The methods and assays can be used as a complement or alternative to oversulfated glycosaminoglycan screening via Nuclear magnetic resonance spectroscopy (NMR). The methods and assays can further be used for removing OS-GAG from various glycosaminoglycans such as heparin.

The binding compound is any molecule that binds to an OS-GAG. It was surprisingly found that a detector protein-enzyme conjugate designed to bind to heparin is able to bind to OS-GAG with a greater affinity as compared to heparin. In an embodiment, the binding compound comprises a heparin binding molecule (HBM) as described by the publication WO 2005/018552 to Prestwich, et al., which is incorporated herein by reference. The HBM can be comprised of one or more individual units, called heparin binding units (HBUs). In certain embodiments, the HBM is a peptide-based molecule, meaning that one or more of the HBU is a peptide-based molecule.

In another embodiment, the binding compound comprises a detector protein in the form of a heparin binding construct (HB3). The HB3 construct is a recombinant fusion protein consisting of three receptor for hyaluronan mediated motility (RHAMM) P1-domains in tandem. More generally, the binding compound can comprise an OS-GAG binding unit or domain, recombinantly expressed as a single domain or as any number of tandem multimers of OS-GAG binding domains.

The detector protein can further be attached to an enzyme such as horseradish peroxidase (HRP) to form a detector protein-enzyme conjugate. Non-limiting examples of suitable detector protein-enzyme conjugates are the glutathione S-transferase (GST) tagged Heparin Binding Protein, the His tagged Heparin Binding Protein, or the Heparin Binding Protein conjugated to HRP sold by Lifespan Technologies, Salt City, Utah.

In an embodiment, the binding compound can comprise a heparin binding unit or HB3 construct that is fused or bound to any suitable component such as an enzyme, an antibody or a combination thereof for detection/identification. In addition to horseradish peroxidase, the enzyme can be alkaline phosphatase, luciferase, or fluorescent protein (e.g. green fluorescent protein, yellow fluorescent protein, etc.). The HB3 construct can be bound to an antibody in an HB3-antibody complex. The antibody can be fused to an enzyme, labeled with a fluorescent molecule (e.g. fluorescein, rhodamine, etc.) or labeled with a radionuclide (e.g. 3H, 14C, 125I, etc.).

The enzyme fused to the antibody can be, horseradish peroxidase, alkaline phosphatase, luciferase, or fluorescent protein (e.g. green fluorescent protein, yellow fluorescent protein, etc.).

In an alternative embodiment, the binding compound can comprise a heparin binding unit or HB3 construct that is labeled with a component such as a fluorescent molecule (e.g. fluorescein, rhodamine, etc.), a radionuclide (e.g. $^3$H, $^{14}$C, $^{125}$I, etc.), biotin or a combination thereof for detection/identification. The biotinylated HB3 construct can be bound in a complex to avidin, streptavidin or avidin/streptavidin variants fused to horseradish peroxidase, alkaline phosphatase, luciferase, a fluorescent protein (e.g. green fluorescent protein, yellow fluorescent protein, etc.). The biotinylated HB3 construct can also be labeled with a fluorescent molecule (e.g. fluorescein, rhodamine, etc.) or labeled with a radionuclide (e.g. $^3$H, $^{14}$C, $^{125}$I, etc.).

In a general embodiment, the present disclosure provides a method for detecting one or more OS-GAGs in a sample. The sample can comprise, for example, a biological material, a pharmaceutical product or a product for human or animal administration/consumption. The method comprises placing the sample onto a support, contacting the sample on the support with a binding compound that attaches to the OS-GAG and forms an OS-GAG-binding compound complex, and detecting an amount of the OS-GAG-binding compound complex on the support.

The support can comprise OS-GAG and/or heparin immobilized on or attached to the support to be used in a competitive enzyme immunoassay. The support can be a microtiter plate, a microassay chip or a combination thereof.

In an embodiment, the binding compound comprises an OS-GAG binding unit. The binding compound can be an HB3 construct, which preferentially binds to OS-GAG, for example, in a competitive assay. The OS-GAG binding unit can be fused to an enzyme such as, for example, horseradish peroxidase to form a binding compound-enzyme conjugate designed to bind to the OS-GAG. The enzyme can subsequently be detected using a suitable chromogenic substrate. The binding compound may also have affinity for other oversulfated glycosaminoglycans (GAGs) and could be used for detection of such GAGs in a similar manner.

In another embodiment, the present disclosure provides a method for detecting one or more OS-GAGs in a heparin sample. The method comprises placing the heparin sample onto a support comprising immobilized heparin and contacting the heparin sample on the support with a binding compound that attaches to the heparin and forms a heparin-binding compound complex. The binding compound also has a greater affinity for attaching to the OS-GAG than to the heparin in the heparin sample and forms an OS-GAG-binding compound complex. As a result, the OS-GAG competes with heparin in the sample and on the support for the available binding compound. The binding compound can be in a fixed amount in a reagent that is mixed with the heparin sample on the support.

The method can further comprise detecting an amount of the heparin-binding compound complex on the support and determining an amount of OS-GAG in the heparin sample based on the amount of the heparin-binding compound complex on the support. The amount of the heparin-binding compound complex on the support can be measured using any suitable calorimetric method and compared to controls (e.g. using diluted standards).

By determining the amount of the heparin-binding compound complex on the support, OS-GAG in the heparin can be detected. For example, in a competitive assay method, the amount of the heparin binding compound complex on the support will be inversely proportional to the amount of OS-GAG in the heparin sample. Because of the affinity of the binding compound for OS-GAG, a higher amount of OS-GAG in the heparin sample will more effectively attach to the binding compound leaving less of the binding compound to attach to the heparin in the sample or on the support. Therefore, less binding compound on the support will be detected, which indicates the presence of OS-GAG in the heparin sample.

In an alternative embodiment, the present disclosure provides an OS-GAG assay comprising a support containing one or more immobilized OS-GAGs, and a binding compound that attaches to the OS-GAG immobilized on the support and forms an OS-GAG-binding compound complex. The support can be in the form of a microtiter plate, a microassay chip or a combination thereof. The binding compound can comprise a heparin binding unit. In an embodiment, the binding compound is an HB3 construct.

In yet another embodiment, the present disclosure provides a method for detecting one or more OS-GAGs in heparin. The method comprises applying the heparin to an assay such as an enzyme immunoassay or an enzyme-linked immunosorbent assay (ELISA). The assay can utilize a binding compound that attaches to the OS-GAG in the assay to form an OS-GAG-binding compound complex. The method can further comprise detecting the OS-GAG-binding compound complex in the assay. The detecting can be performed using any suitable calorimetric assay, a fluorescence assay, bioluminescence assay, and/or radiolabeled assay.

In still another embodiment, the present disclosure provides a method for detecting one or more OS-GAGs in a sample. The method comprises providing a support having heparin bound to the support and combining the sample with a heparin binding reagent on the support. The support can be a 96 well microtiter plate or a microarray. The heparin binding reagent comprises a binding compound that attaches to the heparin on the support and forms a heparin-binding compound complex. The binding compound also has a greater affinity for attaching to any OS-GAG in the sample than the heparin on the support and forms an OS-GAG-binding compound complex.

The method can further comprise incubating the sample with the heparin binding reagent to allow a sufficient amount of time for the formation of the heparin-binding compound complex and the OS-GAG-binding compound complex. After a sufficient time has elapsed, the support can be washed to remove the heparin binding reagent. A substrate can be applied to the support to elicit signal (e.g. a calorimetric signal). The substrate can be a suitable chromogenic substrate such as, for example, tetramethyl benzidine.

The strength of the signal can be detected to determine the presence of the OS-GAG in the sample. For example, the amount of the heparin binding compound complex on the support may be inversely proportional to the amount of OS-GAG in the heparin sample due to the greater affinity of the binding compound for OS-GAG over heparin. Consequently, less binding compound on the support will be detected, which indicates the presence of OS-GAG in the heparin sample.

The signal can be a chromogenic signal, a fluorogenic signal, an electrochemical signal or a combination thereof. Detecting the strength of the signal can be performed using an instrument such as, for example, a spectrophotometer and a spectrofluorometer.

In an alternative embodiment, the present disclosure provides a method of removing one or more OS-GAGs from a sample. The method comprises immobilizing a binding compound that attaches to the OS-GAG, and exposing the binding compound to the sample under conditions that allow for an OS-GAG-binding compound complex formation. The sample can be, for example, heparin, plasma, blood or a combination thereof. Due to the affinity of the binding compound for OS-GAG, the OS-GAG can attach to the binding compound immobilized on the support and be removed from the sample.

The binding compound can be directly or indirectly coupled to a solid-phase support using any suitable method. The solid-phase support can then be used as a capture device for removal of oversulfated glycosaminoglycan from biological products such as, for example, heparin formulations or for removal and/or purification of oversulfated glycosaminoglycan in manufacturing processes.

The binding compound can be immobilized onto any suitable surface. In an embodiment, the binding compound is immobilized by adsorbing it to a solid-phase support such as, for example, SEPHAROSE® activated beads or other suitable resins. The binding compound can also be immobilized to a microtiter plate or a microassay chip.

In yet another embodiment, the present disclosure provides a method of using or administering heparin. The method comprises applying the heparin to an assay. The assay can utilize a binding compound that attaches to an OS-GAG in the heparin to form an OS-GAG-binding compound complex. The method can further comprise detecting the OS-GAG-binding compound complex in the assay and using the heparin as an anticoagulent. For example, if the heparin is determined not to be contaminated with OS-GAG, the heparin can be administered to a patient in need of an anticoagulant.

In still another embodiment, the present disclosure provides a method of manufacturing heparin (e.g. as an active ingredient or final product form). The method comprises contacting the heparin in an active ingredient or final product form with a binding compound that attaches to an oversulfated glycosaminoglycan (OS-GAG) in the heparin to form an OS-GAG-binding compound complex. The binding compound can be in a solution that is mixed with the heparin. The OS-GAG-binding compound complex can be removed from the heparin using any suitable method such as, for example, filtration or ion-exchange. As a result, the manufactured heparin can be free of any OS-GAG contaminants.

Alternatively, the binding compound can also be immobilized on a suitable support such as solid-phase support, a microtiter plate, a microassay chip and combinations thereof. The heparin can contact the support having the immobilized binding compound for any period of time. Once the heparin is moved from the support, the OS-GAG from the heparin will be attached to the binding compound on the support and remain on the support.

OS-GAGs have several therapeutic applications, such as medical implant coatings, use in wound healing and use as anticoagulants. In yet another embodiment, the present disclosure provides a method for manufacturing one or more OS-GAGs comprising contacting an OS-GAG in a carrier with a binding compound that attaches to the OS-GAG to form an OS-GAG-binding compound complex. The carrier can be, for example, a solution containing the OS-GAG (e.g. made by synthesis reactions). The method can further comprise removing the OS-GAG-binding compound complex from the carrier. The binding compound can comprise a heparin binding unit such as an HB3 construct.

In yet another embodiment, the present disclosure provides for a chemical binding apparatus comprising a binding compound attached to a support. The binding compound is capable of attaching to an OS-GAG to form an OS-GAG-binding compound complex. The support can comprise one or more microspheres with the binding compound attached to the microspheres. The chemical binding apparatus can be used in conjunction with any fluids or solutions comprising one or more OS-GAGs. The chemical binding apparatus can also be used, for example, to remove OS-GAGs from any pharmaceutical products or products for human or animal administration/consumption.

In addition to the previously discussed methods and assays, the HB3 construct can be used as a detection reagent for OS-GAGs in cultured cells, fixed cell or other biological samples (e.g. for microscopy applications, etc).

EXAMPLES

By way of example and not limitation, the following examples are illustrative of various embodiments of the present disclosure.

Example 1

It was surprisingly found that an enzyme immunoassay EIA for detecting heparin can also be used to detect certain contaminants in heparin, namely oversulfated chondroitin sulfate A (OSCS-A). The LIFESPAN® (Salt City, Utah) Heparin EIA from Lifespan Technologies was used to assess the relative concentrations of various test and control samples of heparin (test=lots of heparin contaminated with OSCS-A; control=lots of heparin not contaminated with OSCS-A).

The EIA assay is a competitive assay, which utilizes heparin coated microtiter plates. Soluble heparin, incubated in the heparin-coated wells, competes with the heparin coated on the microtiter plates for binding to a soluble heparin binding protein conjugated to horseradish peroxidase (e.g. detector protein-enzyme conjugate). After the incubation period, any unbound soluble heparin binding protein is washed from the microtiter plates, and a chromogenic agent is added to the wells to elicit a colorimetric response from the bound detector protein-enzyme conjugate. The absorbance of each well can be measured to determine the presence of heparin in the solution.

In the absence of heparin, the maximum signal is observed (highest absorbance at 450 nm), because the heparin binding protein will be completely adsorbed to the heparin on the surface of the microtiter plate. However, in the presence of soluble heparin, the amount of detector protein bound to the microtiter plates decreases relative to the concentration of heparin in solution. Heparin standards can be run to generate a standard curve for extrapolation of the concentrations of unknown heparin test samples.

Experimental Procedure

General EIA experimental conditions using the Lifespan® Heparin EIA (Cat: K-2300).

1) All reagents were reconstituted according to the manufacturer's instructions.
2) Test samples were serially diluted in 1:10 steps with phosphate buffered saline (PBS).
3) The test samples were loaded into duplicate wells in the microtiter plate (10 μL sample per well).
4) Detection reagent (i.e. detector protein-enzyme conjugate) was added to all wells (90 μL per well).
5) The microtiter plates were incubated for 30 min at room temperature on a plate shaker rotating @ 450 RPM.
6) The microtiter plates were washed four times with TBS-T (provide with the kit) using an automated plate washer.

7) Tetramethyl benzidine (TMB) substrate was added to all wells (100 µL per well) and incubated 5 min at room temperature shaking @ 450 rpm.
8) The reactions were then stopped with 50 µL of acid stop solution.
9) The microtiter plates were then read at 450 nm on a plate reader.

Results

A USP Heparin Reference Standard (357 U/mL—U.S. Pharmacopeia) was run and the response curve is shown in FIG. 1 to establish a baseline reference for heparin using the LIFESPAN® Heparin EIA. Test lots and control lots of heparin in 1) a final container form (e.g. finished product) and 2) an active pharmaceutical agent (API) form dissolved in PBS were tested. It was unexpectedly found that all test lots had a substantially greater response relative to the control heparin lots as shown by a lack of absorbance. In other words, the detector protein-enzyme conjugate has a greater affinity for the OSCS-A in the test heparin lots than the heparin. Table 1 provides lot information for the test articles.

TABLE 1

Heparin Samples

| Sample # | Test/Ctrl |
|---|---|
| Baxter API C1 | Control |
| Baxter API T1 | Test |
| Baxter API T2 | Test |
| Baxter API T3 | Test |
| Baxter API T4 | Test |
| Baxter API T5 | Test |
| Baxter FC C1 | Control |
| Baxter FC C2 | Control |
| Baxter FC T1 | Test |
| Baxter FC T2 | Test |
| Competitor FC C1 | Control |
| Competitor FC C2 | Control |

TABLE 2

Additional Sample Descriptions

| Sample # | Sample Type |
|---|---|
| Baxter API T5 (Digest) | This sample was digested with heparinase and the heparinase resistant material was purified by filtration. |
| OSCS-A | Oversulfated Chondroitin Sulfate A* |
| OSCS-B | Oversulfated Chondroitin Sulfate B (dermitan sulfate)* |
| USP Heparin Standard | USP Heparin Reference Standard; Lot: LOG091, 357 U/mL |
| OS-Heparin | Oversulfated Heparin* |

Figure 2:
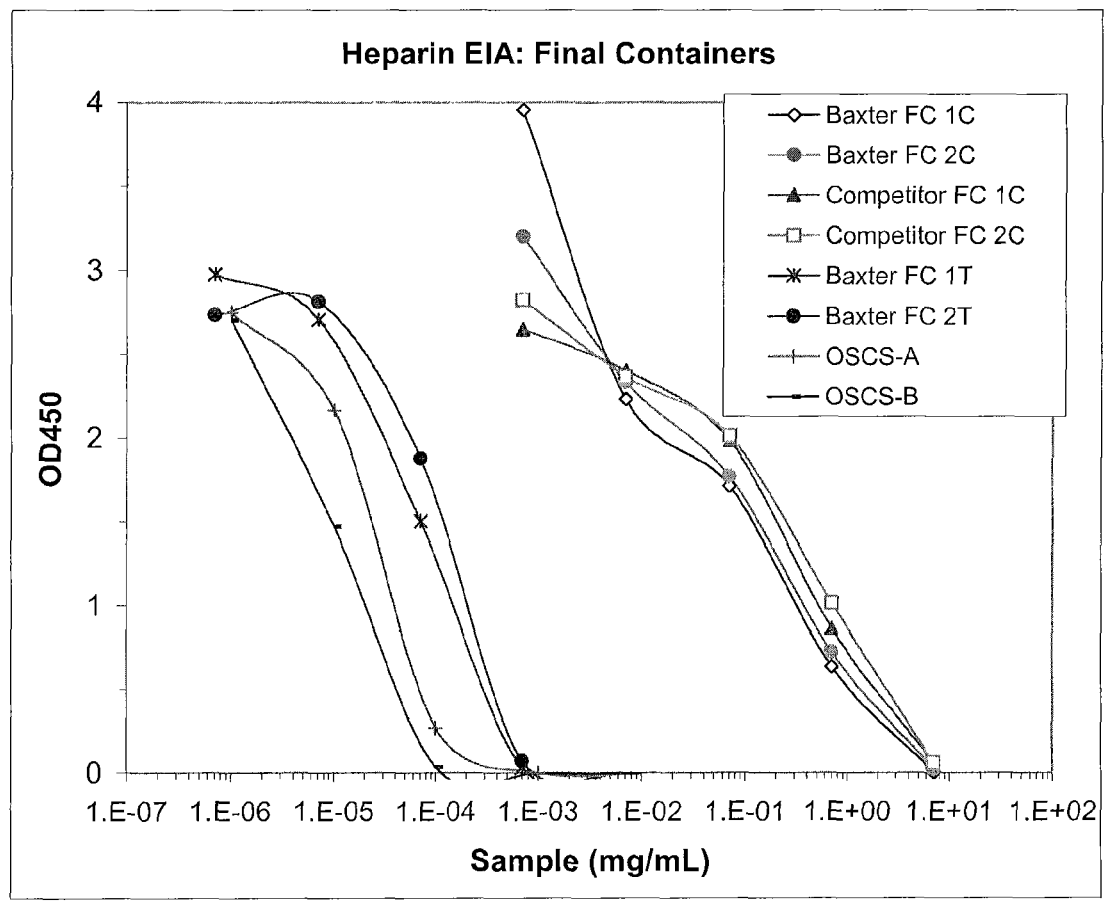
FIG. 2 shows a graph of a response curve for test lots and control lots of heparin in final container form.
Figure 3:
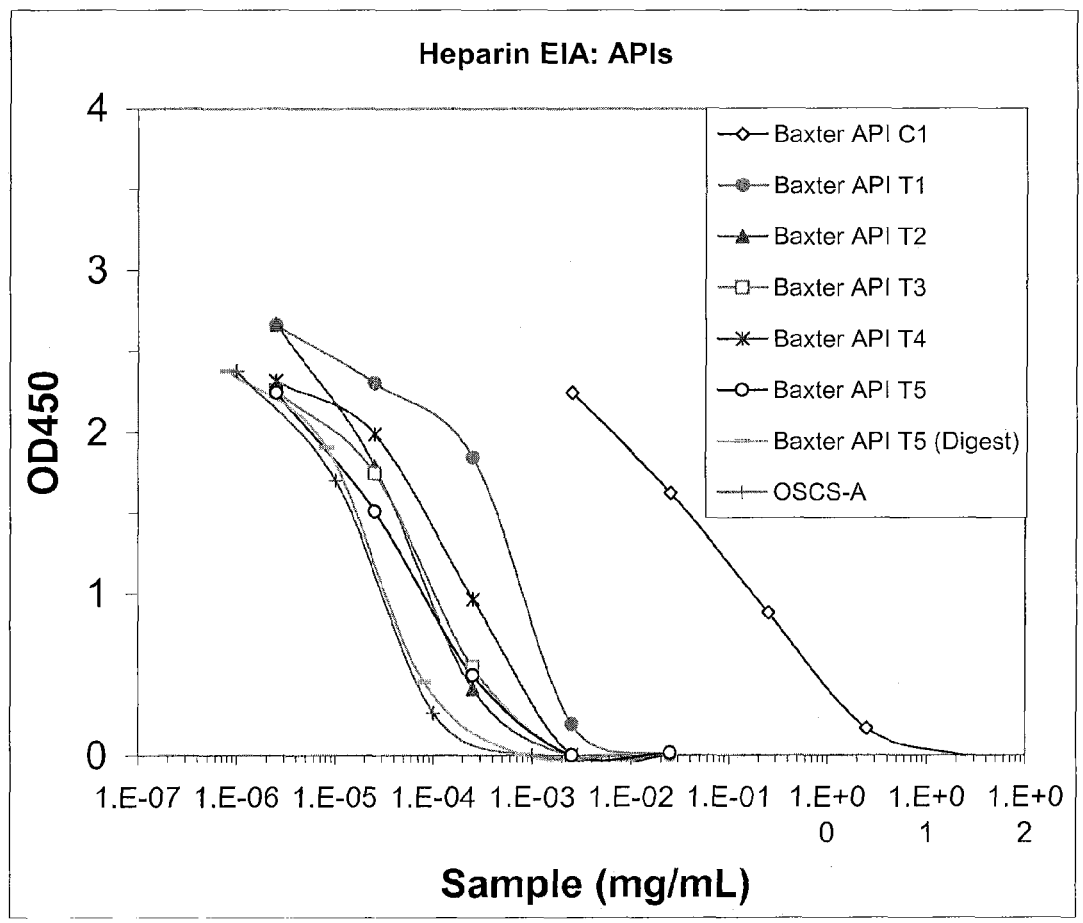
FIG. 3 shows a graph of a response curve for test lots and control lots of heparin in the active pharmaceutical ingredient form.

*synthesized according to Maruyamaa, et al. Carbohydrate Research, 306, pp. 35-43 (1998), which is hereby incorporated by reference The heparin samples were rerun at more appropriate dilutions for better visualization of the complete response curves and are shown in FIGS. 2-3. As shown in FIGS. 2-3, there is approximately a 1000-10000 fold difference in the response between test lots and control lots for heparin in the final container and API form. Additionally, the heparinase resistant material purified from digestion of a test APT (Baxter API T5 (Digest)) had a similar response curve to the other test heparin lots as shown in FIG. 3. The impurity was subsequently identified as OSCS-A.

To confirm that the EIA was preferentially binding to OSCS, OSCS-A and OSCS-B (oversulfated chondroitin sulfate B [dermatan sulfate]) were synthesized. These materials were subsequently tested using the LIFESPAN® Heparin ETA (FIGS. 2-3).

As shown in FIG. 2, the ETA does not distinguish between OSCS-A and OSCS-B (dermatan sulfate), which are empirically identical but differ only in orientation of a carboxyl moiety. However, as shown in FIGS. 2-3, the ETA is approximately 10000 fold more sensitive to the presence of OSCS-A as compared to heparin (as demonstrated by the difference in the response between OSCS-A, purified heparinase resistant API and the test heparin lots as compared to the control lots of heparin). Additionally, FIG. 3 shows that the ETA responses of the purified heparinase resistant material from a test API (Baxter API T5 (Digest)) and that of the synthesized OSCS-A were essentially identical.

Example 2

Figure 4:
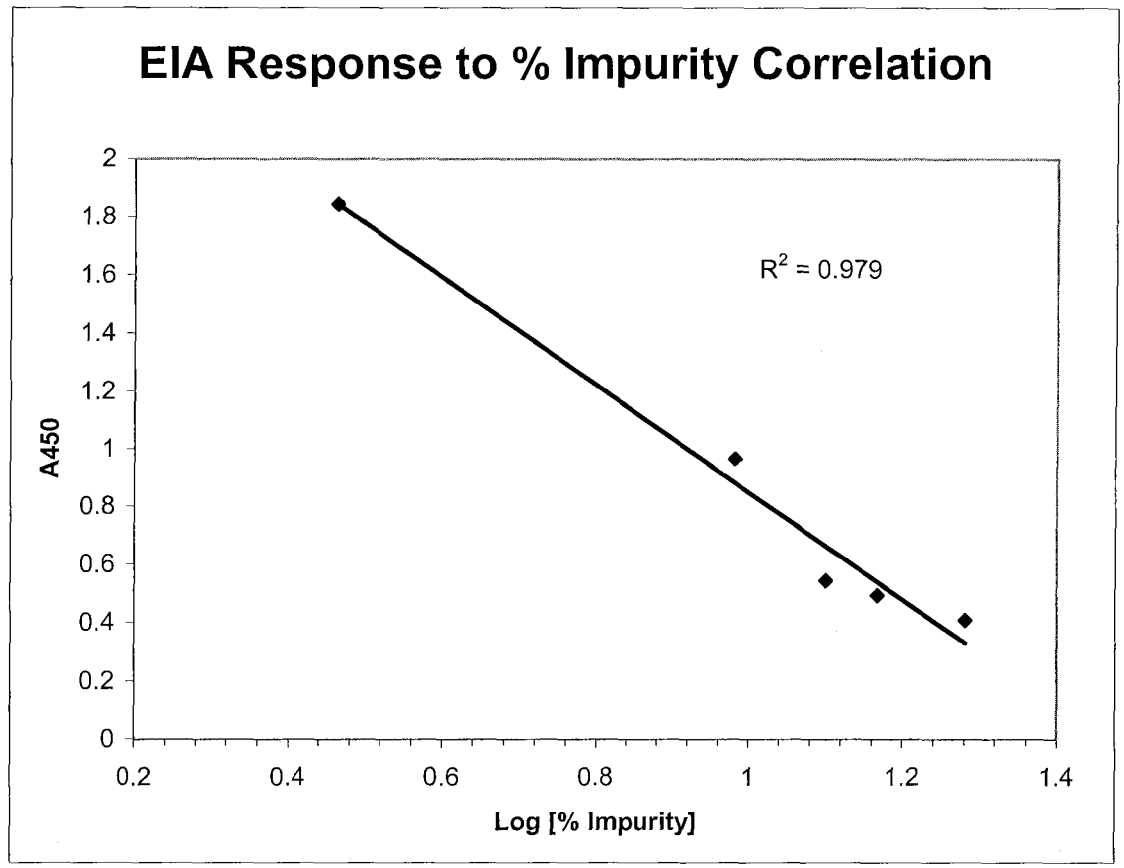
FIG. 4 shows a graph of a response curve of the enzyme immunoassay (EIA) at a dilution of 250 ng/mL of sample for various test lots showing the correlation of the EIA response to the level of contamination (mol % impurity).

The relative level of OSCS-A in the heparin was determined for test lots via NMR (see Table 3). The response of the EIA at a dilution of 250 ng/mL of sample for these various test lots was then plotted and the correlation of the EIA response to the level of contamination (mol % impurity) was determined. As shown in FIG. 4, the EIA has an excellent correlation of response relative to the level of OSCS-A contamination in the heparin test APIs.

TABLE 3

Mol % impurity of OSCS-A in Heparin APIs

| Sample | A450 @ 250 ng/mL | OSCS mol % |
|---|---|---|
| Baxter API T1 | 1.845 | 2.9 |
| Baxter API T4 | 0.967 | 9.6 |
| Baxter API T3 | 0.545 | 12.6 |
| Baxter API T5 | 0.494 | 14.7 |
| Baxter API T2 | 0.409 | 19.1 |

Figure 5:
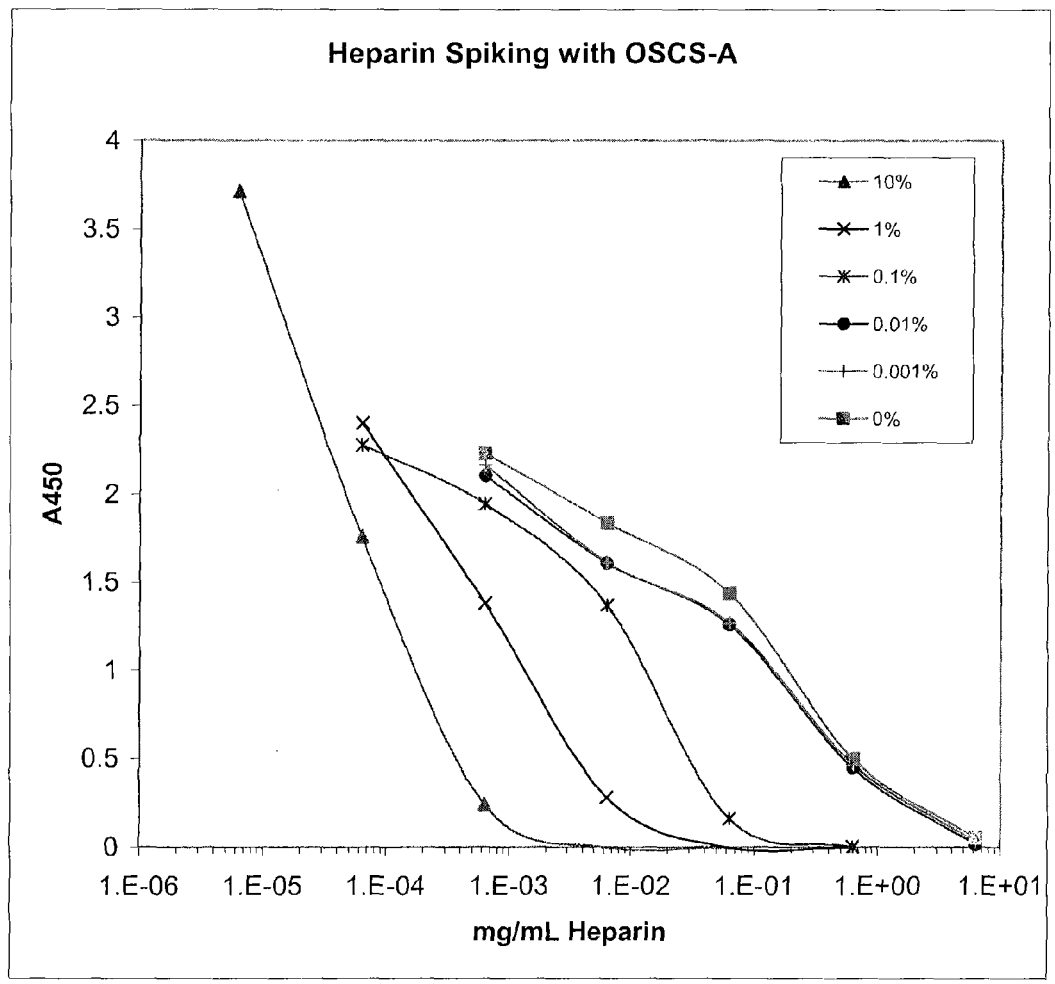
FIG. 5 shows a graph of a response curve for OSCS-A (oversulfated chondroitin sulfate) spiked into control heparin at various concentrations.

In an effort to determine the sensitivity of the EIA for detecting OSCS-A contamination, OSCS-A was spiked into control heparin at various concentrations (expressed as % contamination wt/wt). As shown in FIG. 5, the sensitivity of the EIA for detecting OSCS-A contamination of heparin is between 0.1% and 0.01% by weight, demonstrating the effectiveness of this EIA for detecting very low concentrations of OSCS-A contamination in heparin.

Figure 6:
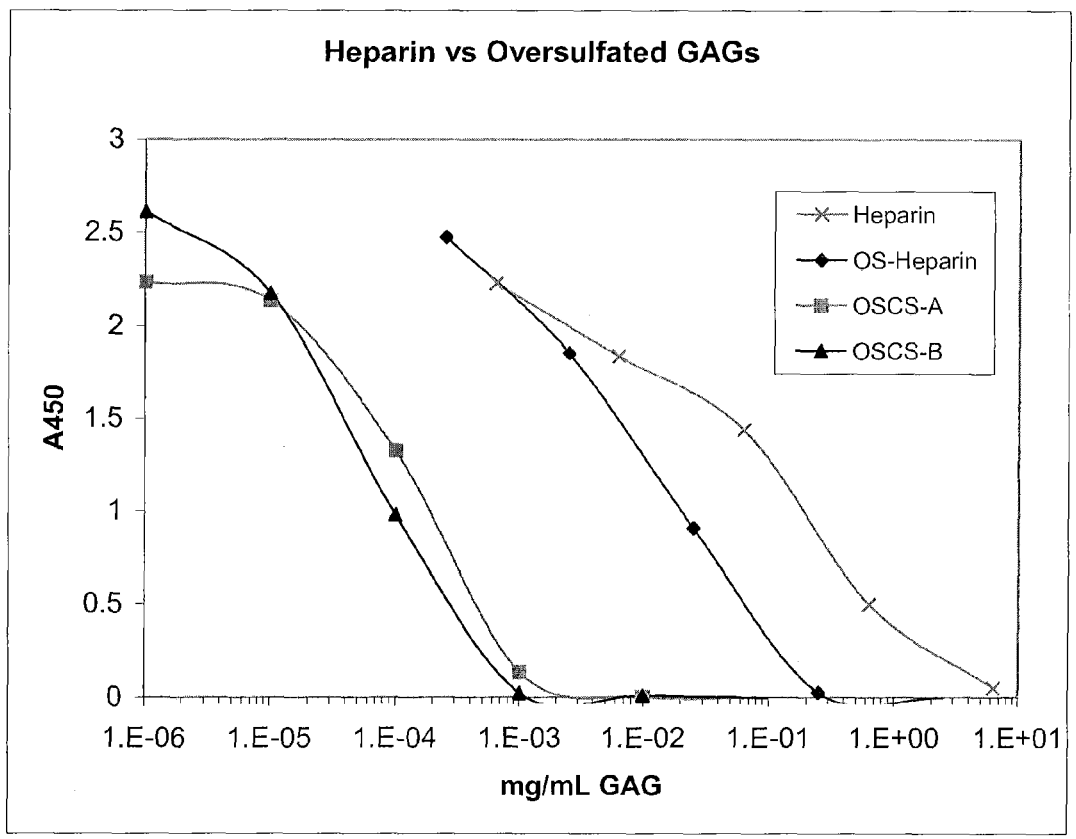
FIG. 6 shows a graph of a response curve showing the relative responses from heparin, OS-heparin, OSCS-A and OSCS-B (dermatan sulfate).

FIG. 6 shows the relative responses from heparin, oversulfated heparin (OS-heparin) and OSCS-A and OSCS-B. EIA preferentially recognizes OSCS-A and OSCS-B over heparin and OS-heparin. OSCS-A and OSCS-B are empirically identical, but differ in the orientation of a carboxyl moiety. There is an approximate 2 log difference in detection level between OSCS and OS-heparin and an approximate 4 log difference between heparin and the OSCSs.

CONCLUSION

The Lifespan® Heparin detection reagent containing a detector protein-enzyme conjugate (derived from the hyaluronan binding domain of RHAMM) has a greater affinity for the heparinase resistant material (i.e. the OSCS-A) present than the heparin in both final container and API lots of heparin. The detector protein-enzyme conjugate binds to OSCS-A with at least 1000 fold greater affinity than to heparin based on initial experiments. Consequently, the detector protein-enzyme conjugate can be used as a screening tool for detection of OSCS-A in biological samples such as heparin. Because the binding of the detector protein-enzyme conjugate is specific to OSCS-A, this detector protein-enzyme The invention is claimed as follows:

1. A method of determining oversulfated chondroitin sulfate ("OS-CS") in a heparin sample, the method comprising:
    placing the heparin sample onto a support;
    contacting the heparin sample on the support with a binding compound comprising an HB3 construct that attaches to the OS-CS and forms an OS-CS-binding compound complex, the binding compound having a stronger affinity for the OS-CS than heparin in the heparin sample; and
    detecting an amount of the OS-CS-binding compound complex on the support.

2. The method of claim 1, wherein the support is selected from the group consisting of a microtiter plate, a microassay chip and combinations thereof.

3. The method of claim 1, wherein the HB3 construct is bound to a component selected from the group consisting of an enzyme, an antibody and combinations thereof.

4. A method of determining oversulfated chondroitin sulfate ("OS-CS") in a heparin sample, the method comprising:
    placing the heparin sample onto a support comprising immobilized heparin;
    contacting the heparin sample on the support with a binding compound comprising an HB3 construct that attaches to heparin in the heparin sample and on the support and forms a heparin-binding compound complex, the binding compound having a greater affinity for attaching to the OS-CS than to the heparin in the heparin sample and forms an OS-CS-binding compound complex;
    detecting an amount of the heparin-binding compound complex on the support; and
    determining an amount of OS-CS in the heparin sample based on the amount of the heparin-binding compound complex on the support.

5. The method of claim 4, wherein the support is selected from the group consisting of a microtiter plate, a microassay chip and combinations thereof.

6. The method of claim 4, wherein the HB3 construct is bound to a component selected from the group consisting of an enzyme, an antibody and combinations thereof.

7. The method of claim 6, wherein the enzyme is horseradish peroxidase.

8. A method of detecting oversulfated chondroitin sulfate ("OS-CS") in a heparin sample, the method comprising:
    applying the heparin sample to an assay utilizing a binding compound comprising an HB3 construct that attaches to an OS-CS in the heparin sample to form an OS-CS binding compound complex, the binding compound having a stronger affinity for the OS-CS than heparin in the heparin sample; and detecting the OS-CS-binding compound complex.

9. The method of claim 8, wherein the assay is selected from the group consisting of colorimetric assay, fluorescence assay, bioluminescence assay, radiolabeled assay and combinations thereof.

10. A method of detecting oversulfated chondroitin sulfate ("OS-CS") in a heparin sample, the method comprising:
    providing a support having heparin bound to the support;
    combining the heparin sample with a heparin binding reagent on the support, wherein the heparin binding reagent comprises a binding compound comprising an HB3 construct that attaches to the heparin on the support and forms a heparin-binding compound complex, the binding compound having a greater affinity for attaching to the OS-CS than to the heparin on the support and forms an OS-CS-binding compound complex;
    incubating the heparin sample with the heparin binding reagent to allow for the formation of the heparin-binding compound complex and the OS-CS-binding compound complex;
    washing the support to remove the heparin binding reagent;
    applying a substrate to the support to elicit signal; and
    detecting the strength of the signal to determine the presence of the OS-CS in the heparin sample.

11. The method of claim 10, wherein the support is a 96 well microtiter plate.

12. The method of claim 10, wherein the substrate is a chromogenic substrate.

13. The method of claim 10, wherein the signal is selected from the group consisting of a chromogenic signal, a fluorogenic signal, an electrochemical signal and combinations thereof.

14. The method of claim 10, wherein the detecting the strength of the signal is performed using an instrument selected from the group consisting of a spectrophotometer and a spectrofluorometer.

15. A method of using heparin, the method comprising:
    applying a heparin sample of the heparin to an assay, wherein the assay utilizes a binding compound comprising an HB3 construct that attaches to an oversulfated chondroitin sulfate ("OS-CS") in the heparin to form an OS-CS-binding compound complex, the binding compound having a stronger affinity for the OS-CS than heparin in the heparin sample;
    detecting the OS-CS-binding compound complex in the assay; and
    administering the heparin to a patient in need of an anticoagulant if the heparin sample is determined not to be contaminated with the OS-CS.

* * * * *